United States Patent [19]
Grob et al.

[11] Patent Number: 4,552,871
[45] Date of Patent: Nov. 12, 1985

[54] STEROIDS OF THE 20-SPIROXANE SERIES, PROCESSES FOR THE MANUFACTURE THEREOF, PHARMACEUTICAL PREPARATIONS CONTAINING SUCH COMPOUNDS AND THE USE OF THE LATTER

[75] Inventors: Jürgen Grob, Giebenach; Jaroslav Kalvoda, Binningen, both of Switzerland

[73] Assignee: Ciba Geigy Corporation, Ardsley, N.Y.

[21] Appl. No.: 598,132

[22] Filed: Apr. 9, 1984

[30] Foreign Application Priority Data

Apr. 13, 1983 [CH] Switzerland ............... 1979/83

[51] Int. Cl.$^4$ .................... A61K 31/58; C07J 9/00
[52] U.S. Cl. ..................... 514/172; 514/175; 260/239.55 R; 260/239.57
[58] Field of Search ............... 260/239.55 R, 239.57, 260/397.1; 424/241

[56] References Cited
U.S. PATENT DOCUMENTS 4,079,054  3/1978  Green et al. ............ 260/239.57
4,118,488  10/1978  Philippson et al. ........ 260/239.57

*Primary Examiner*—Elbert L. Roberts
*Attorney, Agent, or Firm*—Michael W. Glynn

[57] ABSTRACT

(5α)-20-spirox-1-en-3-ones (I) and 17-hydroxy-5α,17α-pregn-1-en-3-ones (II) of the formulae

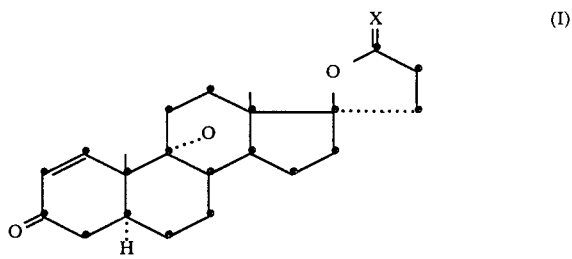

and

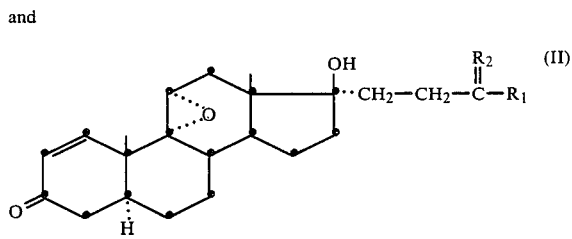

in which X represents O or $H_2$, $R_2$ represents O and $R_1$ represents OH, OMe, OAlk, $NH_2$, $NHR_3$, $NR_3R_4$, or $R_2$ represents $H_2$ and $R_1$ represents OH, OAlk, OAr, OAralk or OAc, in which $R_3$, $R_4$ and Alk represent lower alkyl, Me represents a metal atom or metal equivalent or the cation of an organic base, Ar represents monocyclic aryl, Aralk represents monocyclic aryl-lower alkyl, and Ac represents lower alkanoyl, monocyclic aroyl, lower alkylsulphonyl or monocyclic arylsulphonyl, it being possible for $R_3$ together with $R_4$ also to represent a lower alkylene group optionally interrupted by a hetero atom, are manufactured by known analogy processes. They exhibit an aldosterone-antagonistic action and can therefore be used, for example, as potassium-conserving diuretics, optionally together with another electrolyte-non-specific diuretic or saluretic.

24 Claims, No Drawings

STEROIDS OF THE 20-SPIROXANE SERIES, PROCESSES FOR THE MANUFACTURE THEREOF, PHARMACEUTICAL PREPARATIONS CONTAINING SUCH COMPOUNDS AND THE USE OF THE LATTER

The invention relates to novel (5α)-20-spirox-1-en-3-ones of the formula

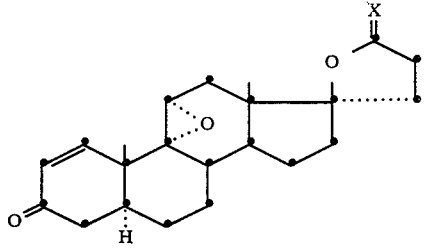

and derivatives thereof having the opened spiro-linked ring in the 17-position, namely 17-hydroxy-5α,17α-pregn-1-en-3-ones of the formula

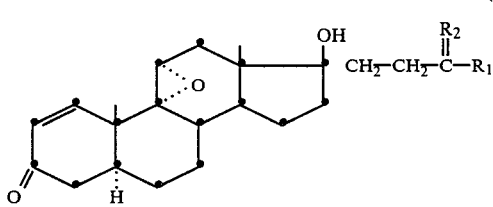

in which

X represents O or $H_2$, $R_2$ represents O and $R_1$ represents OH, OMe, OAlk, $NH_2$, $NHR_3$ or $NR_3R_4$, or $R_2$ represents $H_2$ and $R_1$ represents OH, OAlk, OAr, OAralk or OAc, wherein $R_3$, $R_4$ and Alk represent lower alkyl, Me represents a metal atom or metal equivalent or the cation of an organic base, Ar represents monocyclic aryl, Aralk represents monocyclic aryl-lower alkyl, and Ac represents lower alkanoyl, monocyclic aroyl, lower alkylsulphonyl or monocyclic arylsulphonyl, it being possible for $R_3$ together with $R_4$ also to represent a lower alkylene group optionally interrupted by a hetero atom, and to processes for the manufacture thereof, pharmaceutical preparations that contain these compounds, the therapeutic use of the compounds as potassium-conserving diuretics, and to compositions of the novel compounds with diuretics or saluretics. The invention relates also to the use of the novel compounds in treatments that make use of diuretics and saluretics, in which they are administered at the same time as or in succession with these medicaments.

By "20-spiroxane" there is understood the following ring system

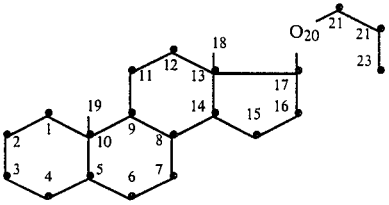

see, for example, British Patent Specification No. 1 041 534. The nucleus on which the above compounds of the formula (I) are based is here termed "(5α)-20-spiroxane". The compound according to formula (I) in which X represents $H_2$ is therefore 9α,11α-epoxy-(5α)-20-spirox-1-en-3-one, and the corresponding compound in which X represents O is 9α,11α-epoxy-(5α)-20-spirox-1-ene-3,21-dione.

Compounds of the formula (II) in which $R_2$ represents O and $R_1$ represents a free or functionally modified hydroxy or amino group include 9α,11α-epoxy-17-hydroxy-3-oxo-5α,17α-pregn-1-ene-21-carboxylic acid, its metal salts or salts with organic bases, and its esters, amides or substituted amides. The compound of the formula (I) in which X represents O is the γ-lactone of the carboxylic acid according to formula (II).

Compounds of the formula (II) in which $R_2$ represents $H_2$ and $R_1$ represents a free or functionally modified hydroxy group include 9α,11α-epoxy-17β-hydroxy-17α-(3-hydroxypropyl)-5α-androst-1-en-3-one and its esters and ethers. The cyclisation product of the free alcohol is the compound of the formula (I) in which X represents $H_2$, that is to say 9α,11α-epoxy-(5α)-20-spirox-1-en-3-one.

The term "lower" as applied to alkyl or alkanoyl groups means that such a radical has from 1 to 7 carbon atoms, for example methyl, ethyl, n-propyl, isopropyl, n-butyl, isobutyl, tert.-butyl, n-pentyl and n-hexyl, or formyl, acetyl, propionyl, butyryl and valeroyl, respectively. Monocyclic aryl is especially phenyl or its substitution derivatives having from 1 to 3 lower alkyl groups, such as, especially, methyl groups, and/or halogen atoms, such as, especially, chlorine or bromine atoms. Monocyclic aryl-lower alkyl is, for example, phenylmethyl or phenylethyl. Monocyclic aroyl is, for example, benzoyl or a radical produced therefrom by substitution with hydroxy, amino or methyl, such as, for example, salicyloyl or anthranoyl. Monocyclic arylsulphonyl is, for example, p-toluenesulphonyl or benzenesulphonyl, and lower alkylsulphonyl is, for example, methyl- or ethyl-sulphonyl. A lower alkylene group preferably has from 2 to 6 carbon atoms and is preferably an alkylene group having a straight carbon chain. Ethers according to the above formula are accordingly derived from lower aliphatic alcohols or, optionally, from monocyclic aromatic alcohols or from monocyclic araliphatic alcohols. The substituted amides contain one or two identical or different lower alkyl radicals or are in ring form and in the latter case are derived, for example, from pyrrolidine or piperidine. Since the alkylene group —$R_3R_4$— can also be interrupted by a hetero atom, such as, especially, nitrogen, oxygen or sulphur, there also come into consideration amides that are derived, for example, from piperazine or morpholine. Metal salts of 9α,11α-epoxy-17-hydroxy-3-oxo-5α,17α-pregn-1-ene-21-carboxylic acid are especially the alkali metal or alkaline earth metal salts, such as the sodium or potassium salt, and also the ammonium salt, the magnesium salt or the calcium salt.

As salts of organic bases, special mention should be made of ammonium salts of suitable, preferably physiologically tolerable, organic nitrogen-containing bases. As bases there come into consideration amines, such as lower alkylamines, for example triethylamine, hydroxy-lower alkylamines, for example 2-hydroxyethylamine, di-(2-hydroxyethyl)-amine or tri-(2-hydroxyethyl)-amine, cycloalkylamines, for example dicyclohexylamine, or benzylamines, for example benzylamine and N,N'-dibenzylethylenediamine, as well as nitrogen-containing heterocyclic compounds, for example those of aromatic character, such as pyridine or quinoline, or those having an at least partially saturated heterocyclic ring, such as N-ethylpiperidine, morpholine, piperazine or N,N'-dimethylpiperazine.

Of the specific compounds according to the invention, in addition to those already referred to there should also be mentioned
9α,11α-epoxy-(5α)-20-spirox-1-ene-3,21-dione
9α,11α-epoxy-(5α)-20-spirox-1-en-3-one
9α,11α-epoxy-17-hydroxy-3-oxo-5α,17α-pregn-1-ene-21-carboxylic acid
9α,11α-epoxy-17-hydroxy-17α-(3-hydroxypropyl)-5α-androst-1-en-3-one,
and ethers and esters thereof that are derived from lower alkanols having from 1 to 4 carbon atoms or from alkanoic acids having from 1 to 4 carbon atoms, respectively, and especially also the potassium, sodium and ammonium salts of 9α,11α-epoxy-17-hydroxy-3-oxo-5α,17α-pregn-1-ene-21-carboxylic acid and the methyl, ethyl and propyl esters thereof and the unsubstituted amide and the mono- or di-methyl-, -ethyl- or -propyla-mides; also the methyl, ethyl and propyl ethers of 9α,11α-epoxy-17-hydroxy-17α-(3-hydroxypropyl)-(5α)-androst-1-en-3-one.

The compounds of the formulae I and II according to the invention are distinguished by advantageous biological properties and are therefore valuable pharmaceutical active ingredients. In particular, they have a strong aldosterone-antagonistic action and can be used therapeutically as potassium-conserving diuretics. Thus, in the Kagawa test on male rats, which have been treated with 1 μg of aldosterone and from which the adrenal gland has been excised, in the case of peroral administration they exhibit an antimineralocorticoidal action in doses of as low as approximately 0.5 mg/kg and have an ED$_{50}$ of between 1 and 10 mg/kg, with a duration of action of approximately 3 to 7 hours. In comparison, the known spironolactone, the strongest commercially available antimineralocorticoid, exhibits in the same test under the same conditions an ED$_{50}$ of approximately 5 mg/kg. The antimineralocorticoidal action of the novel compounds according to the invention therefore appears to be more pronounced than in the case of previously known medicaments of this type. Special mention should be made of the very good tolerability of the novel compounds. In this respect they are superior, for example, to the above-mentioned spironolactone. An anti-androgenic action cannot be demonstrated either in intact or in castrated male rats at doses of up to over 100 mg/kg. Even at doses of 3 mg/kg (300 times the active dose of progesterone), in the McPhail test on rabbits no gestagenic action can be ascertained.

The novel compounds can therefore be used in the treatment of all indications in which an aldosterone-antagonistic action is desirable, for example as potassium-conserving diuretics and as antihypertensives. They can also be used especially in cases of cyrrhosis of the liver and cardiac insufficiency.

The compounds of the formulae I and II according to the invention can be manufactured in a manner known per se. The process for their manufacture according to the present invention is characterised in that (a) a compound corresponding to the formula (III) or (IV)

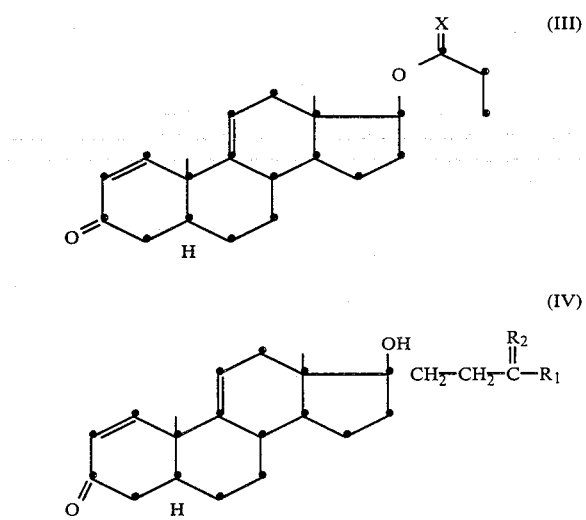

in which X, R$_1$ and R$_2$ have the same meanings as those given for formulae (I) and (II), is oxidised by treatment with a peracid to form the corresponding 9α,11α-epoxide, or (b) in a compound corresponding to the formula (V) or (VI)

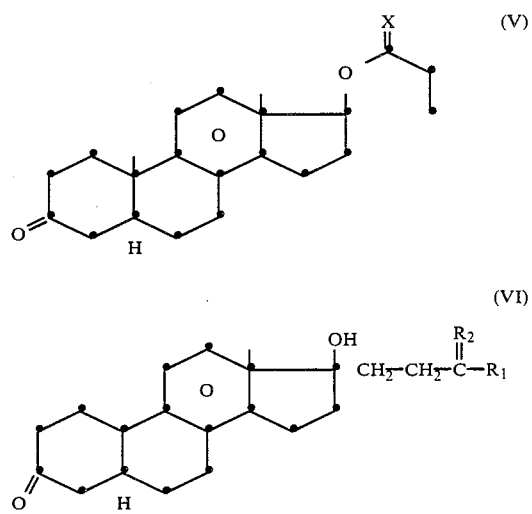

in which X, R$_1$ and R$_2$ have the same meanings as those given for formulae (I) and (II), a double bond is introduced by chemical methods into the 1,2-position, or (c) in a compound corresponding to the formula (VII) or (VIII)

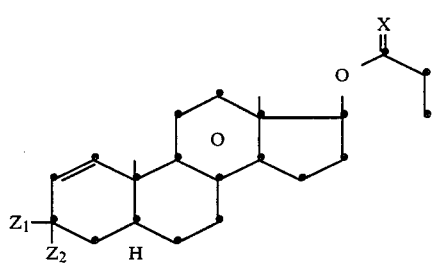

(VII)

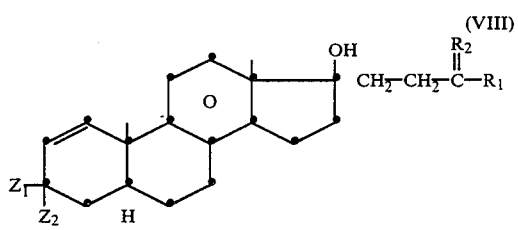

(VIII)

in which X, $R_1$ and $R_2$ have the meanings given above, and $Z_1$ and $Z_2$ represent a grouping that can be converted into the oxo group, the group $Z_1$ and $Z_2$ is converted into the 3-oxo group, or (d) in a compound of the formula (IX)

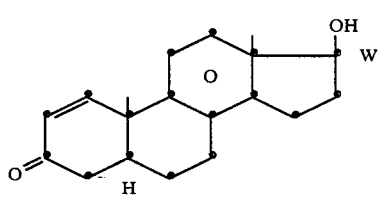

(IX)

in which W represents a propyl group substituted in the 3′-position by a reactive functional group or by a modified group derived therefrom, or represents an ethyl group substituted by a free, esterified or amidated carboxy group, the group W is reacted with the 17β-OH group with the formation of a spiroether or spirolactone ring, or (e) in a compound of the formula (X)

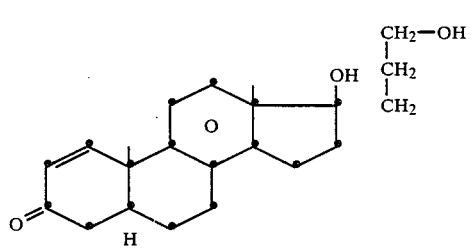

(X)

the carbinol group is oxidised to a carboxy group, optionally with cyclisation with the 17β-hydroxy group, or (f) a compound of the formula (XI)

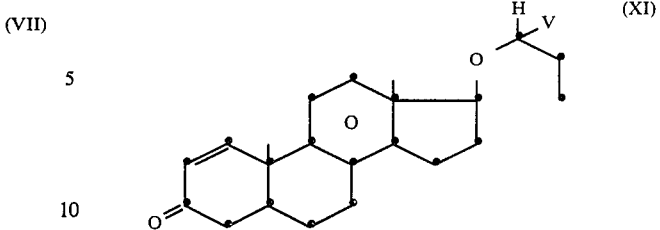

(XI)

in which V represents H or a free, esterified or etherified hydroxy or mercapto group, is oxidised to form the corresponding spirolactone, or (g) in a compound of the formula (XII) or (XIII)

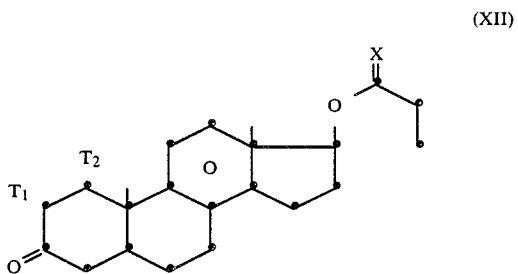

(XII)

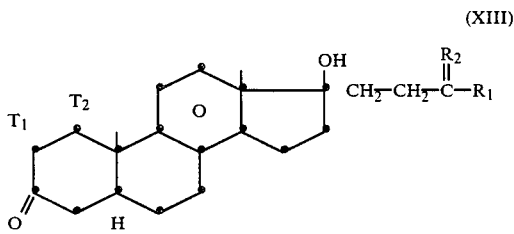

(XIII)

in which X, $R_1$ and $R_2$ have the meanings given above and one of the substituents $T_1$ and $T_2$ is a leaving group and the other represents hydrogen, the leaving group is removed with the formation of the 1,2-double bond, or (h) in a compound of the formula (II) in which a free hydroxy or carboxy group is present in the 17α-side chain, this group is functionally modified or, in a compound of the formula (II) in which a functionally modified hydroxy or carboxy group is present, this group is converted into the corresponding free group, or (i) a compound of the formula (I) in which X represents O is converted into a corresponding carboxylic acid according to formula (II), and, if desired, the 9α,11α-epoxy-17-hydroxy-3-oxo-5α,17α-pregn-1-ene-21-carboxylic acid obtained in accordance with any one of the above processes is converted into one of its metal salts or salts with organic bases, or a salt obtained in accordance with one of the said processes is converted into the free acid.

The above processes can be carried out in a manner known per se.

The epoxidisation according to the process of the 9,11-double bond in compounds of the formula (III) or (IV) in accordance with variant (a) above can be carried out in a manner known per se. It is preferable to use organic peracids, such as perphthalic acid, perbenzoic acid, peracetic acid or m-chloroperbenzoic acid, and to carry out the reaction in an inert solvent, such as, for example, an ether, for example diethyl ether, or an aromatic or a, preferably halogenated, aliphatic hydrocarbon, at low temperature, for example at from 0° to 10° or at room temperature or slightly elevated temperature.

According to variant (b) above of the process according to the invention, a double bond is introduced into the 1,2-position of the starting materials of the formula V or VI, for example according to chemical methods known per se.

Thus, the double bond can be introduced, for example, by treating the starting materials at temperatures between approximately −5° and approximately 150° with a quinone having a dehydrogenating action. This dehydrogenation can be carried out in a manner known per se.

It is preferable to use 2,3-dichloro-5,6-dicyano-1,4-benzoquinone and to carry out the operation at boiling temperature in organic solvents, for example aromatic hydrocarbons, such as benzene, toluene or xylene, lower aliphatic alcohols, such as ethanol, propanol or tert.-butyl alcohol, lower aliphatic esters, such as ethyl acetate, but especially in cyclic ethers, such as dioxan or tetrahydrofuran.

It is also possible to carry out the dehydrogenation using an $\Delta^2$-3-enol ether as starting material. It is preferable to use a lower alkyl enol ether, such as a methyl or ethyl enol ether. It is then possible to effect the same dehydrogenation of an enol ether also with manganese dioxide, preferably in a halogenated hydrocarbon, such as chloroform or dichloromethane, the ether-forming alkyl being removed. The 3-enol ether to be used as starting material can be obtained according to generally known methods, preferably by treating the saturated 3-ketone with a corresponding formic acid orthoester, such as methyl orthoformate or ethyl orthoformate, with acid catalysis, conditions being chosen in which the $9\alpha,11\alpha$-epoxy group is not cleaved.

Another preferred dehydrogenating agent for the introduction of the 1,2-double bond is selenium dioxide and derivatives of selenious acid or of aromatic seleninic acids or selenenyl halides. The dehydrogenation with selenium dioxide is carried out, for example, in a suitable solvent, preferably a tertiary lower aliphatic alcohol having from 1 to 7 carbon atoms, such as, especially, tert.-butyl alcohol or tert.-amyl alcohol, at temperatures of between approximately −5° and approximately 150°, optionally with the addition of a tertiary base, such as pyridine or collidine. It is also possible to proceed in accordance with the so-called "selenium oxide elimination method" according to Reich (Journal of the American Chemical Society 97, [1975], 5434), by producing 2-arylseleno-3-ketone by treatment of the starting material in the form of a metal enolate or an enol ester with a selenating agent, such as, especially, an arylselenyl halide, for example phenylselenyl bromide or chloride, or benzeneselenenyl trifluoroacetate, and oxidising this 2-arylseleno-3-ketone with hydrogen peroxide, sodium periodate, an organic peroxide, such as m-chloroperbenzoic acid, or ozone to form 2-arylselenoxy-3-ketone which even at low temperature breaks up to form $\Delta^1$-3-ketone and phenylselenenious acid. For carrying out this method it is preferable to use the solvents used in the above-mentioned original publication and to observe the conditions specified therein, caution being advisable especially in the oxidation step because of the strongly exothermic reaction.

Another method uses aromatic seleninic acids or derivatives thereof, such as the anhydrides, for example benzeneseleninic acid anhydride. The method is described by T. G. Back in J.C.S. Chem. Commun. 1978, 278–279.

It is also possible to introduce the 1,2-double bond in accordance with the method described by E. Mincione et. al. in "Synthesis 11, 773–774, (1977)" using palladium salts, for example palladium chloride, in a suitable solvent, for example in a lower aliphatic alcohol having from 1 to 7 carbon atoms, such as, especially, in butyl alcohol.

It is also possible to use the methods using oxygen in the presence of metallic catalysts [J. Org. Chemistry, 36, 752, (1971)] or the methods using pyridine N-oxide and acetic anhydride [J. Org. Chemistry, 38, 3737 (1973)].

In accordance with the above-mentioned process method (c) there is used as starting material a compound that contains in the ring A a grouping that can be converted into the 3-oxo group; the conversion is effected in a manner known per se. The mentioned grouping is, for example, a functional derivative of the 3-ketone compounds according to formula (VII) or (VIII) in which $Z_1$ and $Z_2$ represent a functionally modified oxo group. Such starting compounds are, for example, oximes, hydrazones, semicarbazones or ketimines or ketals, thioketals or thiohemiketals. The above-mentioned nitrogen-containing functional derivatives of the ketones can be unsubstituted, such as the free oxime, hydrazone, semicarbazone or ketimine, or can be substituted in the functional moiety, for example by alkyl or alkylene radicals having from 1 to 7 or from 2 to 7 carbon atoms, respectively.

Ketal, thioketal, hemiketal and hemithioketal groups are especially those derived from aliphatic, preferably saturated, alcohols having from 1 to 7 carbon atoms, such as methyl, ethyl or propyl alcohol, butyl or amyl alcohols, or from analogous monocyclic araliphatic alcohols, such as benzyl alcohol. Especially preferred ketals and thioketals are derived from aliphatic dihydric alcohols having from 2 to 4 carbon atoms, such as ethylene glycol or propylene glycol.

In the starting materials of the formula (VII) and (VIII), $Z_1$ and $Z_2$ can also be an enol or enamine group and in this case $Z_2$ represents a 3,4-double bond and $Z_1$ represents a functionally modified hydroxy group. These enol derviatives are especially enol esters, enol ethers, enamines and metal enolates. Enol esters are preferably derived from an aliphatic carboxylic acid having from 1 to 7 carbon atoms, such as from formic, acetic or propionic acid, butyric or valeric acids, or from a simple monocyclic aromatic carboxylic acid, such as benzoic acid or one of its homologues or substitution products. Enol ethers are preferably derived from a lower aliphatic alcohol, for example one of those mentioned above. Enamines are preferably derived from a primary or secondary aliphatic amine having from 1 to 7 carbon atoms or from a simple monocyclic aromatic or araliphatic amine. The following examples of these amines may be mentioned: methyl-, propyl-, isopropyl-, n-butyl-, isobutyl- or tert.-butyl-amine, pyrrolidine, piperidine, aniline, or toluidines and benzylamine. Metal enolate groups are, for example, those of sodium, potassium or lithium enolates.

The group $Z_1$ and $Z_2$ can also be any other ketone-protecting group that can be converted, for example by solvolysis, into the free 3-oxo group.

A group $Z_1$ and $Z_2$ can finally also be a free or functionally modified hydroxy, thiol or amino group together with hydrogen, which group is readily hydrolysed to the 3-oxo group during the oxidation reaction that is to be carried out and intermediately forms the free 3-hydroxy group.

The conversion according to the process of a group $Z_1$ and $Z_2$ into an oxo group can be effected in a manner known per se. Thus, functional derivatives of 3-ketones, such as the above-mentioned oximes, hydrazones, semicarbazones, ketimines, ketals, thioketals, hemiketals and hemithioketals can be converted into the ketones under solvolytic, especially acidic, conditions, for example with dilute mineral acid, such as hydrochloric or sulphuric acid, perchloric acid, oxalic acid or a sulphonic acid, such as, especially, a lower aliphatic sulphonic acid, such as methanesulphonic acid, or a monocyclic aromatic sulphonic acid, such as p-toluenesulphonic acid, or with relatively strong organic acids, such as oxalic or trifluoroacetic acid. Enol derivatives can likewise be converted into the ketones by solvolysis, especially again by the action of acids, but optionally also basically. Conditions must be chosen in which the epoxy group is not cleaved by the action of the acid.

It is preferable to carry out the conversion of thioketals into the 3-ketones with the addition of a sulphur-binding agent, for example a metal salt, especially a heavy metal salt, such as cadmium carbonate and/or mercury(II) chloride. Since the latter agent itself has a strong acid reaction in the presence of water, no additional acid is required as catalyst if it is used. Dethioketalisation is effected especially well by treatment with methyl iodide in acetone at boiling temperature or in a bomb tube at approximately 60°.

The oxidation of a hydroxy, thiol or amino group $Z_1$ or $Z_2$ is likewise effected in a manner known per se, for example by means of compounds of hexavalent chromium, in an acidic or slightly alkaline solution. Thus, oxidation can be effected, for example, with chromium trioxide in the presence of sulphuric acid and optionally acetone or glacial acetic acid or with chromium trioxide in the presence of a tertiary aromatic base, especially pyridine, as long as conditions are chosen that leave the $9\alpha,11\alpha$-epoxy group intact.

The oxidation of the 3-hydroxy group in the 1-dehydrosteroids can, however, also be carried out with an aluminium alcoholate and a ketone, for example in accordance with Oppenauer, for example in toluene, or with manganese dioxide, lead tetraacetate, with dehydrogenation quinones, such as 2,3-dichlorodicyanobenzoquinone, with hypochlorous acid or derivatives thereof, for example bromoacetamide or bromosuccinimide, with bismuth trioxide, oxygen in alkaline solution, copper acetate and similar copper salts. The oxidation proceeds especially well with manganese dioxide in isopropyl alcohol at room temperature.

If, in method (c), $Z_1$ or $Z_2$ is an esterified or etherified hydroxy or thiol group or an acylated amino group, preferably the free functional groups are formed and are oxidised to the oxo group as described above. In several cases it is also possible to oxidise such functionally modified hydroxy groups directly, that is to say if the operation is carried out in acidic solution, since in that case the free functional groups are formed intermediately.

In accordance with method (d) of the process of the present invention, the spirolactone or spiroether ring in the 17-position is produced from $\Delta^1$-17$\alpha$-hydroxyandrostene compounds of the formula (IX) that have in the 17$\alpha$-position a substituted hydrocarbon that is capable of ring formation with the 17$\beta$-hydroxy group.

The cyclisation to form the spiroether in a compound of the formula (IX) in which W represents the group

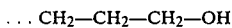
... $CH_2$—$CH_2$—$CH_2$—OH can be effected by means of a sulphonic acid chloride in a tertiary aromatic base, such as especially p-toluenesulphonic acid chloride in pyridine, or analogous reactants [see, for example, J. Med. Chem. 6, 617–618 (1963); U.S. Pat. No. 3,798,213; Tetrahedron Letters (1970), 5057–5059]. The corresponding starting materials can be manufactured according to methods that are described in the articles just mentioned, it of course being necessary to protect intermediately the $\Delta^1$-3-oxo group. A more advantageous method of forming the mentioned spiroether is described in German Offenlegungsschrift No. 2 617 295:

This method is as follows: compounds of the formula (IX) that contain in the 17$\alpha$-position a substituent W of the formula

... $CH_2$—$CH_2$—$CH_2$—$R_o$ in which $R_o$ represents a di-lower alkylamino group, are de-aminated with cyclisation taking place. The deamination is effected, for example, by thermal decomposition of the quaternary bases of the mentioned starting materials. In the "di-lower alkylamino group", the alkyl radicals have a maximum of 7 carbon atoms and are, for example, methyl, ethyl, n-propyl, isopropyl, n-butyl, sec.-butyl, tert.-butyl, a branched or preferably straight-chain pentyl, hexyl or heptyl radical. The de-amination reaction is carried out under the conditions, known per se, of the Hofmann elimination, by converting the di-lower alkylamino compound into the corresponding quaternary tri-lower alkylammonium salt and decomposing this thermally in the form of the corresponding quaternary base. A suitable quaternising agent is a di-lower alkyl sulphate or, especially, a lower alkyl halide, such as a lower alkyl chloride, lower alkyl bromide and, preferably, lower alkyl iodide. A lower alkyl group is especially the methyl group. The quaternisation is carried out in excess alkylating agent or advantageously in an organic solvent, especially a lower alkanol, especially methanol, but also acetone, methyl ethyl ketone or ethyl acetate. The quaternary base is freed from the corresponding salt by means of a strong base. For this purpose there are used strongly basic ion exchangers, silver hydroxide, thallium(I) hydroxide and, especially, alkali metal hydroxides, such as sodium or potassium hydroxide. In the case of sulphates it is also possible to use barium hydroxide. As solvent or diluent there is used water, optionally in the presence of an organic, water-miscible solvent, for example an alcohol, such as a lower alkanol, a lower glycol or glycerine. It is also possible to free the base with a potassium or, especially, sodium, alcoholate, for example one derived from the above-mentioned alcohols. The thermolysis is in practice effected by, for example, concentrating a resulting solution of the quaternary base at increasing temperature and, optionally, under reduced pressure and, if necessary, heating to the point of decomposition, for example to approximately 200°. A particularly advantageous variant consists of adding to the quaternary salt an equimolar quantity of alkali metal hydroxide in aqueous solution, adding ethylene glycol and concentrating the mixture by slow distillation until decomposition is complete. It is advisable to process free quaternary bases only with the careful exclusion of atmospheric carbon dioxide. Further details regarding this method and especially regarding the manufacture of the starting materials can be found in the above-mentioned Offenlegungsschrift. In the manufacture of the starting materials, the $\Delta^1$-3-oxo group is intermediately protected.

Compounds of the formula (I) in which X represents an oxo group can be manufactured in accordance with process variant (d) above from compounds of the formula (IX) in which W represents a free, esterified or amidated carboxyethyl group.

Starting compounds for this process having a free carboxy group can be manufactured analogously to variant (e) mentioned above for the manufacture of process products according to the invention, which process has not yet been discussed. The presence of catalytic amounts of acids is sufficient to cause these starting compounds to cyclise to form the mentioned spirolactones. The esters also enter into this reaction. As starting materials having an amidated carboxy group there are used especially di-lower alkylamides (the alkyl radicals preferably having from 1 to 7 carbon atoms but representing especially methyl). Such compounds can be converted, for example according to the process described in German Offenlegungsschrift No. 24 24 752 by treatment with an acidic cation exchanger to form the spirolactones. The starting material is dissolved in a suitable solvent, such as, for example, an aromatic hydrocarbon, for example benzene, toluene, xylene, an ether, such as diethyl ether, dibutyl ether, dioxan, tetrahydrofuran or diethylene glycol dimethyl ether, a halogenated hydrocarbon, such as methylene chloride, chloroform or dichloroethylene, but also in ethyl acetate, pyridine, dimethylformamide, dimethyl sulphoxide, in alcohols, such as methanol or ethanol, or ketones, such as acetone or methyl ethyl ketone, and is added to the acidic cation exchanger. The reaction is generally complete at room temperature after from 5 to 25 hours. It can also be carried out at elevated temperature, so that the reaction period is reduced, if required, to only approximately 2 hours.

The starting materials can be manufactured according to the methods mentioned in the above-mentioned patent specification.

In accordance with process variant (e), the compounds of the formula (X) are oxidised to form compounds of the formula (I) or (II). The oxidation to form the carboxylic acid or the spirolactone can be effected in one step by means of strong oxidising agents, such as chromic acid or derivatives thereof, for example chromium trioxide, in acidic solution, for example in sulphuric acid, optionally in the presence of acetone and/or acetic acid, or in basic solution, for example chromium trioxide-pyridine; alternatively the oxidation can be effected in stages by first manufacturing the corresponding aldehyde according to methods known per se, for example by way of the corresponding nitrons, or with copper(II) salts in alkaline solution, and oxidising this aldehyde in a manner known per se to form the acid, which operation can be carried out in a manner known per se, for example with chromium(VI) compounds.

In accordance with process variant (f), for example compounds of the formula (XI) in which V represents H are oxidised to form the corresponding spirolactone. This can advantageously be effected in a manner known per se with ruthenium tetroxide [Journal of the American Chemical Society 80, 6682, (1958), J. Organic Chemistry 28, 2729 (1963)] or tert.-butyl chromate (Tetrahedron Letters No. 58, 5057–5059).

In accordance with the same variant it is also possible, however, to use compounds of the formula (XI) in which V represents a free, esterified or etherified hydroxy group. Such compounds are hemiacetals or hemithioacetals of aldehydes of the formula

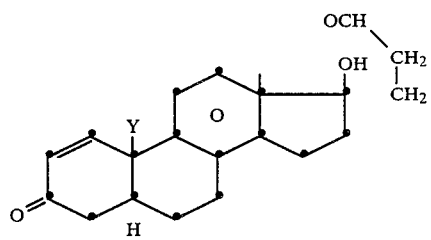

and the esters and ethers thereof. These are oxidised in accordance with the process of variant (f) in a manner known per se to form the compounds of the formula I in which X represents O.

The oxidation can also be carried out with those oxidising agents that are capable in acidic solution of oxidising an aldehyde to form the corresponding carboxylic acid, it being necessary to maintain conditions under which the $9\alpha,11\alpha$-epoxy group is not cleaved. Especially suitable are chromium trioxide in acidic solution, especially in lower alkanecarboxylic acids as solvent, or chromiumsulphuric acid in acetone, and also nitric acid or nitrous acid, or nitroxides, hypohalites, especially hypochlorous or hypobromous acid, N-bromosuccinimide or N-chlorosuccinimide in acidic solution, permanganate or peracids, such as peracetic acid, perbenzoic acid, m-chloroperbenzoic acid or perphthalic acid. The oxidation is generally carried out in inert organic solvents, such as lower aliphatic carboxylic acids, ketones, ethers, dimethyl sulphoxide or chlorinated hydrocarbons, such as methylene chloride, chloroform, or carbon tetrachloride. It is also possible to add water and this is advantageous if nitric acid, nitrous acid or potassium permanganate are used as oxidising agents. The temperature is maintained at between approximately 0° and 80°. The starting materials can be manufactured analogously to the known processes for the manufacture of corresponding compounds unsubstituted in the 9,11-position, for example as described in the following patent specifications:

| German Offenlegungsschrift | 2 237 143 |
| " | 2 248 834 |
| " | 2 248 835 |
| " | 2 251 476 |
| " | 2 625 723. |

As indicated, for example, in Offenlegungsschrift No. 2 237 143, the cyclohemiacetals or thioacetals that are to be used as starting materials and that are already substituted in rings A and B according to formula XI, can be manufactured by reaction of a corresponding 17-ketone that contains in the A-ring a group that can be converted into the $\Delta^1$-3-oxo group with an organometal derivative of the formula

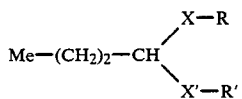

(Me = for example, alkali metal)

in which X and X' represents oxygen or sulphur and R and R' represents a hydrocarbon radical having from 1 to 20 carbon atoms, preferably from 1 to 10 carbon atoms, and in which R and R' can also be bonded to one another so that together with the atoms X and X' and the —CH group they form a ring, in which case R and R' preferably contain from 2 to 6 carbon atoms, and solvolysis of the resulting condensation product. In resulting free cyclohemiacetals the hydroxy group can be esterified or etherified either simultaneously with the solvolysis step or subsequently thereto, this being effected by the addition of an alcohol, for example one of the above-mentioned lower aliphatic alcohols. The ether formation is catalysed by small quantities of acid. The esterification of the resulting aldehyde hemiacetals is also readily initiated if they are brought into contact with the desired acid. It is thus possible to manufacture the acetates or thioacetates of the cyclic hemiacetals, for example, by treatment with acetic acid or thioacetic acid at temperatures of between approximately room temperature and 100°.

After the condensation of the 17-ketone with the mentioned organometal compound and, optionally, after the said solvolysis and/or esterification or etherification, the $\Delta^1$-3-oxo group can be formed from the mentioned group that can be converted into the said oxo group.

In accordance with variant (g), in compounds of the formula (XII) or (XIII) in which a leaving group $T_1$ or $T_2$ is present in the 1- or 2-position, this group can be removed with the formation of a double bond. Such a leaving group is especially a free or esterified hydroxy or mercapto group, or a halogen atom, especially bromine, chlorine or iodine. 1α- or 2α-hydroxy compounds can be manufactured in a manner known per se, for example by microbiological methods. Especially advantageous leaving groups are hydroxy groups esterified by a carboxylic acid or, especially, by a sulphonic acid, for example an aliphatic sulphonic acid having from 1 to 7 carbon atoms or a monocyclic aromatic sulphonic acid, such as methanesulphonic acid, benzene- or p-toluenesulphonic acid. The removal of such a group is effected, for example, by the action of a basic reagent, such as, especially, a tertiary base, such as pyridine or collidine, or an inorganic base, especially a salt of a lower aliphatic carboxylic acid having a basic action, such as sodium acetate. From a free 1-hydroxy or 2-hydroxy compound it is possible to form the double bond in the 1,2-position under the conditions of the Oppenauer oxidation, for example in the oxidation of a 1,3-diol.

An especially advantageous variant of this method uses from starting materials of the formula XII or XIII in which $T_1$ represents a halogen atom and $T_2$ represents H. $T_1$ is in this case especially chlorine or iodine, but more especially bromine. Such compounds are obtained by halogenation of the corresponding unsubstituted compounds, for example with elemental halogen, for example bromine, or with suitable agents that yield bromine, such as, for example, perbromides of organic tertiary nitrogen bases or of ethers, such as pyridine perbromide or dioxan perbromide.

The dehydrohalogenation of starting materials halogenated in this manner is effected with basic agents, such as, for example, tertiary aromatic bases, such as pyridine or quinoline, or homologues thereof, such as collidine, or aliphatic bases, or cycloaliphatic bases, such as tri-lower alkylamines, for example the so-called Hunig base, ethyl diisopropylamine. The reaction can be carried out in an inert solvent, for example in a chlorinated aliphatic hydrocarbon, for example methylene chloride, ethylene chloride, carbon tetrachloride or chloroform, or in a ketone, such as acetone or methyl propyl ketone or cyclohexanone, or in an ester, such as ethyl acetate or an ether, such as dioxan or tetrahydrofuran, at temperatures between room temperature and approximately 150°. The dehydrohalogenation can, however, also be effected with inorganic bases, such as, especially, with basic salts of alkali or alkaline earth metals or of magnesium, for example potassium, sodium or ammonium salts of aliphatic carboxylic acids having from 1 to 7 carbon atoms, such as those of acetic acid, propionic acid, butyric acids or valeric acids, or lithium, and especially also with a lithium halide, such as lithium chloride or bromide, in the presence of an alkali or alkaline earth metal carbonate, such as calcium carbonate. As solvent it is possible to use in this case too one of those given special mention above, such as an ether, for example tetrahydrofuran, but also a lower aliphatic dialkylamide, such as dimethylacetamide, or a sulphoxide, such as dimethyl sulphoxide. When using basic salts of alkalis or alkaline earth metals that are derived from organic acids, there is advantageously used as reactant or solvent the corresponding organic acid, for example acetic acid if sodium acetate is used [see, for example, U.S. Pat. No. 3,076,001—Gazz. Chim. Ital. 93, 10705 (1963)].

The functional modification of a hydroxy group or of a carboxy group in accordance with process variant (h) can likewise be carried out in a manner known per se. Suitable agents for the etherification of the hydroxy group are, for example, diazo compounds, such as optionally substituted diazo-lower alkanes, for example diazomethane, diazoethane and diazo-n-butane. These reagents are used in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran.

Of the known methods of etherification mentioned hereinbelow there are suitable those which can be used under conditions that leave the 9α,11α-epoxide group intact. As etherifying agents there come into consideration especially esters of corresponding alcohols with strong inorganic or organic acids, such as mineral acids, for example hydrohalic acids, such as hydrochloric, hydrobromic or hydriodic acid, and also sulphuric acid, or halosulphuric acid, for example fluorosulphuric acid, or strong organic sulphonic acids, such as lower alkanesulphonic acids optionally substituted, for example, by halogen, such as fluorine, or aromatic sulphonic acids, such as, for example, benzenesulphonic acids optionally substituted by lower alkyl, such as methyl, halogen, such as bromine, and/or by nitro, for example methanesulphonic, trifluoromethanesulphonic or p-toluenesulphonic acid. Such esters are, inter alia, lower alkyl halides, di-lower alkyl sulphates, such as dimethyl sulphate, and also fluorosulphonic acid esters, such as lower alkyl esters, for example fluorosulphonic acid methyl ester, or optionally halo-substituted methanesulphonic acid lower alkyl esters, for example trifluoromethanesulphonic acid methyl ester. They are customarily used in the presence of an inert solvent, such as an optionally halogenated, such as chlorinated, aliphatic, cycloaliphatic or aromatic hydrocarbon, for example methylene chloride, an ether, such as dioxan or tetrahydrofuran, or a mixture. It is preferable to use suitable condensation agents, such as alkali metal carbonates or bicarbonates, for example sodium or potassium carbonate or bicarbonate (customarily together with a sulphate), or organic bases, such as preferably sterically hindered tri-lower alkylamines, for example N,N-diisopropyl-N-ethylamine (preferably together with halosulphonic acid lower alkyl esters or optionally halo-substituted methanesulphonic acid lower alkyl esters), the operation being carried out while cooling, at room temperature or while heating, for example at temperatures from approximately $-20°$ to approximately 50° C. and, if necessary, in a closed vessel and/or under an inert gas atmosphere, for example a nitrogen atmosphere.

The above-described etherification reaction can be considerably accelerated by phase transfer catalysis [see Dehmlow, Angewandte Chemie, Vol. 5, page 187 (1974)]. As phase transfer catalysts there may be used quaternary phosphonium salts and, especially, quaternary ammonium salts, such as optionally substituted tetraalkylammonium halides, for example tetrabutylammonium chloride, bromide or iodide, or alternatively benzyl triethylammonium chloride, in catalytic or up to equimolar amounts. As organic phase there may be used any water-immiscible solvent, for example one of the optionally halogenated, such as chlorinated, lower aliphatic, cycloaliphatic or aromatic hydrocarbons, such as tri- or tetra-chloroethylene, tetrachloroethane, carbon tetrachloride or chlorobenzene, or toluene or xylene. The alkali metal carbonates or bicarbonates, for example potassium or sodium carbonate or bicarbonate, alkali metal phosphates, for example potassium phosphate, and alkali metal hydroxides, for example sodium hydroxide, that are suitable as condensation agents can be added to the reaction mixture by titration, for example by means of an automatic titration apparatus, so that the pH value during etherification remains between approximately 7 and approximately 8.5.

Further etherifying agents are suitable acetal compounds, for example gem-di-lower alkoxy-lower alkanes, such as 2,2-dimethoxypropane, which are used in the presence of strong organic sulphonic acids, such as p-toluenesulphonic acid, and a suitable solvent, such as a di-lower alkyl or lower alkylene sulphoxide, for example dimethyl sulphoxide, or are suitable orthoesters, for example orthoformic acid tri-lower alkyl esters, for example orthoformic acid triethyl ester, which are used in the presence of a strong mineral acid, for example sulphuric acid, or a strong organic sulphonic acid, such as p-toluenesulphonic acid, and a suitable solvent, such as an ether, for example dioxan.

Further etherifying agents are corresponding trisubstituted oxonium salts (so-called Meerwein salts) or disubstituted carbenium or halonium salts, in which the substituents are the etherifying radicals, for example tri-lower alkyloxonium salts, and di-lower alkoxycarbenium or di-lower alkylhalonium salts, especially the corresponding salts with complex fluorine-containing acids, such as the corresponding tetrafluoroborates, hexafluorophosphates, hexafluoroantimonates or hexachloroantimonates. Such reagents are, for example, trimethyloxonium or triethyloxonium hexafluoroantimonate, hexachloroantimonate, hexafluorophosphate or tetrafluoroborate, dimethoxycarbenium hexafluorophosphate or dimethylbromonium hexafluoroantimonate. These etherifying agents are preferably used in an inert solvent, such as an ether or a halogenated hydrocarbon, for example diethyl ether, tetrahydrofuran or methylene chloride, or in a mixture thereof, if necessary in the presence of a base, such as an organic base, for example a preferably sterically hindered tri-lower alkylamine, for example N,N-diisopropyl-N-ethylamine, and while cooling, at room temperature or while gently heating, for example at from approximately $-20°$ to approximately 50° C., if necessary in a closed vessel and/or under an inert gas atmosphere, for example a nitrogen atmosphere.

Further etherifying agents are finally corresponding 1-substituted 3-aryltriazene compounds in which the substituent is the etherifying radical and aryl preferably represents optionally substituted phenyl, for example lower alkylphenyl, such as 4-methylphenyl. Such triazene compounds are 3-aryl-1-lower alkyltriazenes, for example 3-(4-methylphenyl)-1-methyltriazene, 3-(4-methylphenyl)-1-ethyltriazene or 3-(4-methylphenyl)-1-isopropyltriazene. These reagents are customarily used in the presence of inert solvents, such as optionally halogenated hydrocarbons or ethers, for example benzene, or solvent mixtures, and while cooling, at room temperature and preferably at elevated temperature, for example at from approximately 20° to approximately 100° C., if necessary in a closed vessel and/or under an inert gas atmosphere, for example a nitrogen atmosphere.

For the esterification of the hydroxy group, the starting material of the formula (IV) is treated with an acylating agent that introduces the desired acyl radical of an organic carboxylic acid under conditions that leave the $9\alpha,11\alpha$-epoxide group intact. There is used in the esterification the corresponding carboxylic acid or a reactive derivative thereof, especially an anhydride, including a mixed or internal anhydride of such an acid. Mixed anhydrides are, for example, those with hydrohalic acids, that is to say the corresponding acid halides, especially chlorides, and also with hydrocyanic acid, or those with suitable carbonic acid semiderivatives, such as corresponding semiesters (such as the mixed anhydrides formed, for example, with a haloformic acid lower alkyl ester, such as chloroformic acid ethyl ester or isobutyl ester), or with optionally substituted, for example halogen-containing, such as chlorine-containing, lower alkanecarboxylic acids (such as the mixed anhydrides formed with pivalic acid chloride or trichloroacetic acid chloride). Internal anhydrides are, for example, those of organic carboxylic acids, that is to say ketenes, such as ketene or diketene, or those of carbamic or thiocarbamic acids, that is to say isocyanates or isothiocyanates. Other reactive derivatives of organic carboxylic acids that can be used as acylating agents are activated esters, such as suitably substituted lower alkyl esters, for example cyanomethyl ester, or suitably substitued phenyl esters, for example pentachlorophenyl or 4-nitrophenyl esters. The esterifcation can, if necessary, be carried out in the presence of suitable condensation agents: when using free carboxylic acids, for example, in the presence of carbodiimide compounds, such as dicyclohexyl carbodiimide, or carbonyl compounds, such as diimidazolylcarbonyl, and when using reactive acid derivatives, for example, in the presence of basic agents, such as tri-lower alkylamines, for example triethylamine, or heterocyclic bases, for example pyridine or 4-dimethylaminopyridine. The acylation reaction can be carried out in the absence or presence of a solvent or solvent mixture, while cooling, at room temperature or while heating, and, if necessary, in a closed vessel and/or under an inert gas atmosphere, for example a nitrogen atmosphere. Suitable solvents are, for example, optionally substituted, especially optionally chlorinated, aliphatic, cycloaliphatic or aromatic hydrocarbons, such as benzene or toluene, it being possible to use suitable esterification reagents, such as acetic anhydride, also as diluents.

The compounds of the formula (I) in which X represents O can be converted in a manner known per se into carboxylic acids according to formula (II) or, in accordance with process variant (i), into their salts, by treatment with a base, for example an alkali or alkaline earth metal base. From the carboxylic acid salts that are obtained initially by treatment with a base, the free acids may be freed by acidification. As alkali or alkaline earth metal bases there are used, for example, corresponding hydroxides, such as sodium and, especially, potassium hydroxide, carbonates, such as sodium or potassium carbonate and/or sodium or potassium bicarbonate; as reaction medium there is advantageously used mixtures of water with one or more organic solvents, preferably with those which are water-miscible, for example lower alkanols, such as methanol, ethanol or isopropyl alcohol, cyclic ethers, such as tetrahydrofuran or dioxan, lower alkanones, such as acetone or 2-butanone, or lower alkylamides of lower aliphatic acids, and of these especially N,N-dimethylformamide. Preferably, no more than an equivalent amount of base is used and vigorous reaction conditions are avoided. The same reaction conditions are used also in the conversion of a carboxylic acid according to formula (II) obtained according to any process into its metal salts. For the manufacture of salts with organic bases there are used similar methods known per se, for example an equivalent of the base in question is added to the carboxylic acid in aqueous or organic aqueous medium at room temperature or slightly elevated temperature, and the salt is isolated according to known methods, for example by precipitation or freeze-drying.

The salts obtained according to any one of processes (a) to (i), such as the alkali metal or alkaline earth metal salts, can be converted into the corresponding free 17β-hydroxy-21-pregnenecarboxylic acids by acidifying a solution or suspension of the salt in water or a water-containing organic solvent. Free 17β-hydroxy-21-pregnenecarboxylic acids according to formula II can, if desired, also be converted into salts with a corresponding base: in this manner there are produced especially ammonium salts and salts of organic bases, for example of those mentioned at the beginning.

The starting materials required for the above-described process variants can be manufactured in a manner known per se. Compounds of the formulae (III) and (IV) can be obtained by dehydration of corresponding compounds that are saturated in the 9,11-positions and contain an α- or β-hydroxy group in the 11-position. The dehydration of such 11α- or 11β-hydroxy-(5α)-20-spirox-1-en-3-ones or -3,21-diones or of 11β,17-dihydroxy-3-oxo-5α,17α-pregn-1-ene-21-carboxylic acid or of the corresponding isomeric 11α-hydroxy-21-carboxylic acid and the functional derivatives thereof and of 11β,17β-dihydroxy-17α-(3-hydroxypropyl)-5α-androst-1-en-3-one and the functional derivatives thereof can be effected according to any of the processes known for steroids of the pregnane or androstane series, for example with an organic nitrogen base, such as pyridine or collidine, in the presence of an aliphatic or aromatic sulphonic acid halide, such as, for example, p-toluenesulphonyl chloride, at room temperature or at slightly reduced temperature. An advantageous reagent for removing the mentioned 11β- or 11α-hydroxy group with the formation of the 9,11-double bond is piperidino-sulphur trifluoride, which is preferably used at low temperature, for example between −40° and −60°, in an inert solvent, such as a chlorinated aliphatic hydrocarbon.

The above-mentioned 11α- or 11β-hydroxy derivatives can in turn be obtained from corresponding compounds that are saturated in the 1,2-position according to the same processes as those described above for process variant (b), for example by bromination and dehydrobromination. The saturated derivatives just mentioned can in turn be obtained according to one of the manufacturing methods known for spirolactones and spiroxenes, starting from analogous 5α-H-starting materials that already contain in the 11-position an oxygen function, especially an 11α- or 11β-hydroxy group, and in the 3-position a hydroxy group or a different group that can be converted into the 3-keto group. Thus, for example, 3,11α- or 3,11β-di-hydroxy-5α-androstan-17-one can be reacted in the presence of lithium or magnesium with a γ-chloropropionaldehyde acetal of the formula

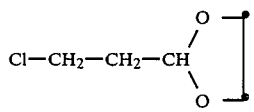

or with an organometal derivative, for example in accordance with the above-mentioned German Offenlegungsschrift No. 2 237 143, to form a compound of the formula

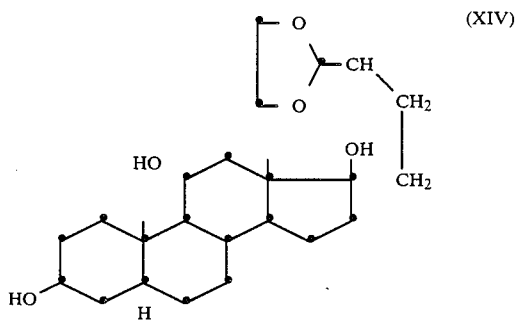

which can then be converted into the desired spirolactone according to the procedure of German Offenlegungsschrift No. 2 237 143. If the above-mentioned 3,11α- or 3,11β-dihydroxy-5α-androstan-17-one is reacted in the same manner with a chloropropyl alcohol derivative, such as a reactive ester, there are obtained compounds analogous to the compounds of the above formula (XIV) and having a functionally modified 3- hydroxypropyl radical in the 17α-position, which can be converted into the spiroxanes having a saturated A ring, 3-keto group and 11β- or 11α-hydroxy group.

The starting materials of the formulae (III)–(XIII) are novel and the present invention relates also to these. Such compounds also include especially compounds according to formula II in which, however, $R_2$ represents O and $R_1$ represents H, or

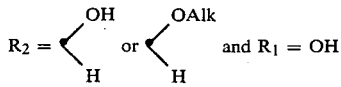 and $R_1 = OH$ in which Alk represents a lower alkyl group in the sense defined above. Such compounds include 9α,11α-epoxy-17-hydroxy-3-oxo-5α,17α-pregn-1-ene-21-carbaldehyde or 9α,11α-epoxy-17β-hydroxy-17α-(3-oxopropyl)5α-androst-1-en-3-one, or its hemiacetals of lower alkanols.

Novel intermediates are also compounds according to formula (I) in which

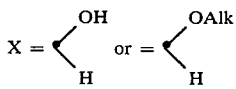

in which Alk has the definition given immediately above, and which include the cyclic hemiacetal of the afore-mentioned aldehyde with the 17β-hydroxy group or its lower alkyl ethers.

The invention relates also to those forms of the above-described processes in which a compound obtainable as intermediate at any stage is used as starting material and the remaining process steps are carried out or in which a starting material is formed under the reaction conditions.

The pharmacologically acceptable compounds of the present invention of the formulae I and II can be used, for example, for the manufacture of pharmaceutical preparations, for example for the treatment of hyperaldosteronism of the most varied forms, which contain an effective amount of the active ingredient alone or in admixture with inorganic or organic, solid or liquid pharmaceutically acceptable carriers that are suitable especially for enteral, for example oral, and parenteral administration. There are preferably used tablets or gelatine capsules that contain the active ingredient together with diluents, for example lactose, dextrose, saccharose, mannitol, sorbitol, cellulose and/or glycine, and lubricants, for example silica, talc, stearic acid or salts thereof, such as magnesium or calcium stearate, and/or polyethylene glycol; tablets can also contain binders, for example magnesium aluminium silicate, starches, such as maize, wheat, rice or arrowroot starch, gelatine, tragacanth, methylcellulose, sodium carboxymethylcellulose and/or polyvinylpyrrolidone, and, if desired, distintegrators, for example starches, agar, alginic acid or a salt thereof, such as sodium alginate, and also effervescent mixtures, absorption agents, colourings, flavourings and sweeteners. Injectable preparations are preferably isotonic aqueous solutions or suspensions; suppositories are especially fatty emulsions or suspensions. The pharmacological preparations can be sterilised and/or contain adjuncts, for example preservatives, stabilisers, wetting agents and/or emulsifiers, solubilisers, salts for regulating osmotic pressure and/or buffers. The present pharmaceutical preparations which, if desired, may contain other pharmacologically valuable substances, are manufactured in a manner known per se, for example by means of conventional mixing, granulating or confectioning processes, and contain from approximately 0.1% to approximately 75%, especially approximately 1% to 50%, of active ingredient. The recommended daily dose for a warm-blooded animal weighing approximately 75 kg is from 10 to 600 mg.

The present invention relates also to compositions containing (A) at least one compound of the formula (I) or (II) according to the present invention, and (B) at least one diuretic that is non-specific with regard to electrolyte excretion, optionally together with pharmaceutical carriers.

By a diuretic that is non-specific with regard to electrolyte excretion there is to be understood a diuretic which excretes both sodium and potassium ions in increased amounts. The presence of the potassium-conserving component A in the above-characterised compositions neutralises the undesirable potassium-excreting action of such diuretics.

As the diuretic component B that is non-specific with regard to electrolyte excretion there come into consideration, for example, classic diuretics or mixtures thereof that increase diuresis both by a renal and by an extrarenal action on the tissues, especially substances having an inhibitory effect on the reabsorption in the tubules, such as saluretics or ethacrynic acid and analogues thereof.

Special mention should be made of benzothiadiazine derivatives, such as thiazides and hydrothiazides, and also benzenesulphonamides, phenoxyacetic acids, benzofuran-2-carboxylic acids and 2,3-dihydrobenzofuran-2-carboxylic acids.

The electrolyte-non-specific component B can comprise a single active ingredient or an advantageous combination of several active ingredients, it being possible for the active ingredients to belong to several of the mentioned groups of substances.

Especially suitable thiazides are, for example, 6-chloro-7-sulphamyl-1,2,4-benzothiadiazine 1,1-dioxide, 6-trifluoromethyl-7-sulphamyl-1,2,4-benzothiadiazine 1,1-dioxide and 2-benzylthiomethyl-6-chloro-7-sulphamyl-1,2,4-benzothiadiazine 1,1-dioxide.

Especially suitable hydrothiazides are, for example, 3-ethyl-6-chloro-7-sulphamyl-3,4-dihydro-1,2,4-benzothiadiazine 1,1-dioxide; 3-trichloromethyl-6-chloro-7-sulphamyl-3,4-dihydro-1,2,4-benzothiadiazine 1,1-dioxide; 3-benzyl-6-trifluoromethyl-7-sulphamyl-3,4-dihydro-1,2,4-benzothiadiazine 1,1-dioxide; 2-methyl-3-(2,2,2-trifluoroethylthiomethyl)-6-chloro-7-sulphamyl-3,4-dihydro-1,2,4-benzothiadiazine 1,1-dioxide; 3-(2,2,2-trifluoroethylthiomethyl)-6-chloro-7-sulphamyl-3,4-dihydro-1,2,4-benzothiadiazine 1,1-dioxide; 3-(5-norbornen-2-yl)-6-chloro-7-sulphamyl-3,4-dihydro-1,2,4-benzothiadiazine 1,1-dioxide; 2-methyl-3-chloromethyl-6-chloro-7-sulphamyl-3,4-dihydro-1,2,4-benzothiadiazine 1,1-dioxide; 6-chloro-7-sulphamyl-3,4-dihydro-1,2,4-benzothiadiazine 1,1-dioxide; 3-dichloromethyl-6-chloro-7-sulphamyl-3,4-dihydro-1,2,4-benzothiadiazine 1,1-dioxide; 3-cyclopentylmethyl-6-chloro-7-sulphamyl-3,4-dihydro-1,2,4-benzothiadiazine 1,1-dioxide; 6-trifluoromethyl-7sulphamyl-3,4-dihydro-1,2,4-benzothiadiazine 1,1-dioxide and 3-isobutyl-6-chloro-7-sulphamyl-3,4-dihydro-1,2,4-benzothiadiazine 1,1-dioxide.

Especially suitable benzenesulphonamides are, for example, 2-chloro-5-N-methylsulphonamidobenzenesulphonamide; 2-chloro-5-N,N-dimethylsulphonamidobenzenesulphonamide; 2-chloro-5-piperidinosulphonylbenzenesulphonamide; 2-chloro-5-(N-carboxymethyl-N-methyl)sulphonamidobenzenesulphonamide; 2-chloro-5-(N-furfurylsulphonamido)-benzenesulphonamide; 2-chloro-5-(N-tetrahydrofurfurylsulphonamido)-benzenesulphonamide; 2-chloro-5-[N-methyl-N-(2-methyl-4-oxotetrahydrofurfuryl)-sulphonamido]-benzenesulphonamide; 4,5-dichlorobenzene-1,3-disulphonamide; 4-chloro-6-methylbenzene-1,3-disulphonamide; 4-chloro-6-aminobenzene-1,3-disulphonamide; 2-chloro-5-methylsulphonylbenzenesulphonamide; 2-chloro-5-ethylsulphonylbenzenesulphonamide; 2-chloro-5-n-butylsulphonylbenzenesulphonamide; 2-methyl-5-ethylsulphonylbenzenesulphonamide; 2-methyl-5-methylsulphonylbenzenesulphonamide; 2-methyl-5-n-butylsulphonylbenzenesulphonamide; 2-chloro-4-(N,N-dibenzylamino)-5-carboxybenzenesulphonamide; 2-furfurylamino-4-chloro-5-N-(p-aminophenyl)-sulphamoylbenzoic acid; 2-furfurylamino-4-chloro-5-N-(O-aminophenyl)-sulphamoylbenzoic acid and especially 3-sulphonamido-4-chlorobenzoic acid; 3-sulphonamido-4-chlorobenzamide; 3-(N-methylsulphamoyl)-4-chloro-N-methylbenzamide; 1-chloro-4-[N-methyl-N-(2-methyltetrahydrofurfuryl)-sulphamoyl]benzenesulphonamide; 1,3-disulphamoyl-4-chlorobenzene; 2-chloro-5-[3-hydroxy-1-oxoisoindolyl-(3)]-benzenesulphonamide; 2-ethyl-4-oxo-6-sulphamoyl-7-chloro-1,2,3,4-tetrahydroquinazoline; 1-oxo-2-cyclohexyl-5-chloro-6-sulphamoyl-1,2-dihydroisoindole; 2-chloro-5-[N-(2,6-dimethylpiperidino)-carbamoyl]-benzenesulphonamide; 2-chloro-4-furfurylamino-5-carboxybenzenesulphonamide and 2-chloro-4-benzylamino-5-carboxybenzenesulphonamide.

Especially suitable phenoxyacetic acids are, for example:

(a) [2,3-dimethyl-4-(2-methylenebutyryl)-phenoxy]acetic acid, [2-methyl-3-chloro-4-(2-methylenebutyryl)-phenoxy]-acetic acid, [4-(2-methylenebutyryl)-1-naphthoxy]-acetic acid and, especially, [2,3-dichloro-b 4-(2-methylenebutyryl)-phenoxy]-acetic acid;

(b) 4-thenoyl-2,3-dichlorophenoxyacetic acid, 4-(5-methylthenoyl)-2,3-dichlorophenoxyacetic acid and 4-furoyl-2,3-dichlorophenoxyacetic acid, and (c) (1-oxo-2-methyl-2-phenyl-6,7-dichloro-5-indanyloxy)-acetic acid (especially as a racemate or the laevo-form), or alternatively [1-oxo-2-(4-chlorophenyl)-6,7-dichloro-5-indanyloxy]-acetic acid and [1-oxo-2-(2-thienyl)-6,7-dichloro-5-indanyloxy]-acetic acid.

Especially suitable benzofuran-2-carboxylic acids are, for example, 5-(2-methylenebutyryl)-6-methylbenzofuran-2-carboxylic acid, 5-(2-methylenebutyryl)-6-methoxybenzofuran-2-carboxylic acid and 5-(2-methylenepropionyl)-6-methylbenzofuran-2-carboxylic acid.

Especially suitable 2,3-dihydrobenzofuran-2-carboxylic acids are, for example, 5-(2-methylenebutyryl)-6-methyl-2,3-dihydrobenzofuran-2-carboxylic acid; 5-(2-methylenebutyryl)-6-fluoro-2,3-dihydrobenzofuran-2-carboxylic acid; 5-(2-methylenebutyryl)-6-chloro-2,3-dihydrobenzofuran-2-carboxylic acid; 5-(2-methylenepropionyl)-6-methyl-2,3-dihydrobenzofuran-2-carboxylic acid; 5-(2-methylenehexanoyl)-6-methyl-2,3-dihydrobenzofuran-2-carboxylic acid; 5-(2-methylenevaleryl)-6-methyl-2,3-dihydrobenzofuran-2-carboxylic acid; 5-(2-methylenepropionyl)-6-methyl-2,3-dihydrobenzofuran-2-carboxylic acid; 5-(2-ethylidenebutyryl)-6-methyl-2,3-dihydrobenzofuran-2-carboxylic acid; 5-(2-methylenebutyryl)-6-methyl-2,3-dihydrobenzofuran-2-carboxylic acid methyl ester; 5-(2-methylenebutyryl)-6-methyl-2,3-dihydrobenzofuran-2-carboxylic acid ethyl ester; 5-(2-methylenebutyryl)-6-methyl-2,3-dihydrobenzofuran-2-carboxylic acid n-butyl ester; 5-(2-methylenebutyrl)-6-methyl-2,3-dihydrobenzofuran-2-carboxylic acid 2-hexyl ester; 5-(2-methylenebutyryl)-6-methyl-2,3-dihydrobenzofuran-2-carboxylic acid n-decyl ester; 5-(2-methylenebutyryl)-6-methyl-2,3-dihydrobenzofuran-2-carboxylic acid cyclopentyl ester; 5-(2-methylenebutyryl)-6-methyl)-2,3-dihydrobenzofuran-2-carboxylic acid cyclohexyl ester; 5-(2-methylenebutyryl)-6-methyl-2,3-dihydrobenzofuran-2-carboxylic acid benzyl ester; 5-(2-methylenebutyryl)-7-methyl-2,3-dihydrobenzofuran-2-carboxylic acid methyl ester; 5-(2-methylenebutyryl)-6-chloro-7-methyl-2,3-dihydrobenzofuran-2-carboxylic acid methyl ester; 5-(2-methylenepropionyl)-6-methyl-2,3-dihydrobenzofuran-2-carboxylic acid methyl ester; 5-(2-methylenevaleryl)-6-methyl-2,3-dihydrobenzofuran-2-carboxylic acid methyl ester; 5-(2-methylene-3-methylbutyryl)-6-methyl-2,3-dihydrobenzofuran-2-carboxylic acid methyl ester; and 5-(2-methylenebutyryl)-6-fluoro-2,3-dihydrobenzofuran-2-carboxylic acid methyl ester, and especially 5-(2-methylenebutyryl)-6,7-dimethyl-2,3-dihydrobenzofuran-2-carboxylic acid; 5-(2-methylene-3-methylbutyryl)-6-methyl-2,3-dihydrobenzofuran-2-carboxylic acid; 5-(2-methylenebutyryl)-6-chloro-7-methyl-2,3-dihydrobenzofuran-2-carboxylic acid.

According to the number of asymmetrical carbon atoms they contain, the mentioned diuretics may be in the form of isomeric mixtures, pure isomers (racemates) or optical antipodes. They are preferably used in the form of the isomer or antipode having the better activity or the lesser toxicity.

The mentioned diuretics having basic groups can also be in free form or in the form of their non-toxic salts. As such salts there come into consideration especially salts with organic or inorganic acids, such as, for example, hydrohalic acids, sulphuric acids, phosphoric acids, nitric acid, perchloric acid, aliphatic, alicyclic, aromatic or heterocyclic carboxylic or sulphonic acids, such as formic, acetic, propionic, succinic, glycolic, lactic, malic, tartaric, citric, ascorbic, maleic, hydroxymaleic or pyruvic acid; phenylacetic, benzoic, p-aminobenzoic, anthranilic, p-hydroxybenzoic, salicylic or p-aminosalicylic acid, methanesulphonic, ethanesulphonic, hydroxyethanesulphonic or ethylenesulphonic acid; halobenzenesulphonic, toluenesulphonic or naphthalenesulphonic acid or sulphanilic acid; cyclohexylsulphamic acid, methionine, tryptophan, lysine or arginine.

The mentioned diuretics having acidic groups can also be in free form or in the form of their non-toxic salts. As such salts there come into consideration especially salts with bases, such as those mentioned at the beginning in connection with compounds of the formulae I and II. Aluminium salts, for example salts from two moles of acid and one mole of aluminium hydroxide, are also suitable, especially because they are resorbed relatively slowly, have no odour and cause negligible gastrointestinal disturbance.

The invention relates also to the manufacture of the compositions and medicaments according to the invention, and to the use of the mentioned combinations of active substances A and B, both in the form of the mentioned compositions and medicaments and by the combined or separate administration of the two active substances, for the treatment of illnesses that involve the impaired excretion of urine or urine constituents, such as, especially, water and electrolytes.

Especially valuable are pharmaceutical compositions and medicaments that contain the aldosterone-antagonistic component A according to the invention and, as component B, 1-oxo-3-(3-sulphamyl-4-chlorophenyl)-3hydroxyisoindoline, 6chloro-7-sulphamyl-3,4-dihydro-1,2,4-benzothiadiazine 1,1-dioxide, 3-cyclopentylmethyl-6-chloro-7-sulphamyl-3,4-dihydro-1,2,4-benzothiadiazine 1,1-dioxide, 4-(2-methylenebutyryl)-2,3-dichlorophenoxyacetic acid, 4-thenoyl-2,3-dichloro-phenoxyacetic acid, [1-oxo-2-methyl-2-phenyl-6,7-dichloro-5-indanyloxy)-acetic acid, 2-chloro-4-furfurylamino-5-carboxybenzenesulphonamide, 2-phenoxy-2-butylamino-5-carboxybenzenesulphonamide or 2-phenoxy-3-[3-(1-pyrrolyl)-propyl]-5-carboxybenzenesulphonamide.

In the pharmaceutical compositions and medicaments according to the invention, the ratio of component A to component B, in relation to the average effective dose in each case, is from approximately 4:1 to approximately 1:4, preferably from approximately 3:2 to approximately 2:3. Since the average effective dose of each specific component is a known value or a value that can be determined in simple manner by known pharmacological test methods, it is readily possible for the person skilled in the art to prescribe within the above-mentioned limits a suitable ratio of the two components for each patient in accordance with the patient's specific disorder, general state of health, individual responsiveness, age and species. The size of the dosage units of the medicaments according to the invention naturally also depends especially on the activity of the particular component A or B, as is preferably expressed by the daily dosage. The term "dosage unit" in this connection is used to denote separate individual portions of a uniform composition that are suitable for medicinal administration and which each contain a specific quantity of the active ingredients according to the invention that corresponds to from approximately 0.05 to approximately 2, preferably from approximately 0.15 to approximately 1, daily dose(s).

Thus, for example, the above-mentioned especially preferred preparations can contain per dosage unit from 15 to 150 mg, especially from 20 to 100 mg, of one of the mentioned compounds as component A. The content of component B is, for example, from 10 to 100 mg, especially from 25 to 50 mg, of 2-chloro-5-[3-hydroxy-1-oxoisoindolyl-(3)]-benzenesulphonamide or 4-(2-methylenebutyryl)-2,3-dichlorophenoxyacetic acid, from 5 to 50 mg, especially from 12 to 25 mg, of 6-chloro-7-sulphamyl-3,4-dihydro-1,2,4-benzothiadiazine 1,1-dioxide or 2-chloro-4-furfurylamino-5-carboxybenzenesulphonamide, from 2 to 20 mg, especially from 5 to 10 mg, of 2-phenoxy-3-[3-(1-pyrrolyl)-propyl]-5-carboxybenzenesulphonamide, from 0.1 to 1.0 mg, especially from 0.25 to 0.5 mg, of 3-cyclopentylmethyl-6-chloro-7-sulphamyl-3,4-dihydro-1,2,4-benzothiadiazine 1,1-dioxide or 2-phenoxy-3-butylamino-5-carboxybenzenesulphonamide, from 100 to 400 mg, especially 200 mg, of 4-thenoyl-2,3-dichlorophenoxyacetic acid and from 5 to 25 mg, especially 10 mg, of racemic (1-oxo-2-methyl-2-phenyl-6,7-dichloro-5-indanyloxy)-acetic acid, or half the amount of the laevo-form of this acid.

For the treatment of oedema, in a case of moderate severity there are taken daily, for example, from 1 to 3 dosage units that contain amounts by weight of the active ingredients that lie at the upper limit of the above-mentioned especially preferred dosage; a moderately severe case of essential hypertonia is treated, for example, with from 1 to 3 dosage units the active ingredient content of which lies at the lower limit of the especially preferred amounts.

In the following Examples, which further illustrate the invention but do not limit the invention, temperatures are given in degrees Centigrade.

EXAMPLE 1

1.4 g of (5α)-20-spiroxa-1,9(11)-diene-3,21-dione are dissolved in 28 ml of methylene chloride; 1.4 g of 90% m-chloroperbenzoic acid are added and the mixture is left to stand at room temperature for two and a half hours. After diluting with methylene chloride, the mixture is washed once in each case with an approximately 10% potassium iodide solution and an approximately 10% sodium thiosulphate solution and then with ice-cold 1N sodium hydroxide solution. After drying, the organic phase is concentrated by evaporation under a water-jet vacuum. The crystalline residue is chromatographed over 50 times the amount by weight of silica gel. Using a toluene/acetone (90:10) mixture there is eluted the pure 9α,11α-epoxy-(5α)-20-spirox-1-ene-3,21-dione which, after once dissolving and crystallising from methylene chloride/ether, has a melting point of 275°–277°. In the above-mentioned Kagawa test this compound has an $ED_{50}$ of from 3 to 5 mg/kg p.o.. The starting material can be manufactured as follows:

At an internal temperature of −50°, 1.65 ml of piperidino-sulphur trifluoride are added over a period of 30 seconds to a solution of 1.57 g of 11α-hydroxy-(5α)-20-spirox-1-ene-3,21-dione in 30 ml of chloroform, and the mixture is then stirred for 30 minutes at an internal temperature of −40°. 31.4 ml of water are added to the reaction solution and the whole is stirred for 5 minutes without cooling. After further dilution with water and chloroform, the organic phase is washed once in each case with ice-cold 1N sodium hydroxide solution and ice-cold 2N hydrochloric acid, dried, and concentrated by evaporation under a water-jet vacuum. Using silica gel chromatography (50 times the amount by weight) there is eluted using a toluene/ethyl acetate (92:8) mixture (5α)-20-spiroxa-1,9(11)-diene-3,21-dione which, after dissolving and crystallising from methylene chloride/ether, melts at 218°–219°.

The 11α-hydroxy-(5α)-20-spirox-1-ene-3,21-dione can be manufactured in the following manner:

11.2 g of lithium metal (in small pieces) and 112 ml of β-chloropropionaldehyde ethyl acetal are added to a solution, cooled to approximately 0°, of 89.6 g of 3β,11α-dihydroxy-(5α)-androstan-17-one diacetate in 4 liters of absolute tetrahydrofuran, and the whole is stirred for 3 hours while cooling with ice and for a further 15 hours at room temperature. After pouring onto approximately 12 liters of ice-water, extraction is carried out twice with chloroform, whereupon the organic phases are washed in succession twice with ice-cold dilute hydrochloric acid and then with water, dried, and concentrated by evaporation under a water-jet vacuum. For the purpose of subsequent acetylation, the resulting yellow oil is dissolved in 500 ml of pyridine and 500 ml of acetic anhydride and left to stand overnight at room temperature. After pouring onto approximately 6 liters of ice-water and stirring for 1 hour, extraction is carried out twice with chloroform. The organic phases are washed twice in each case with dilute ice-cold hydrochloric acid, dilute ice-cold sodium hydroxide solution and water, dried, and concentrated under a water-jet vacuum. The resulting solution of approximately 500 ml is filtered through aluminium oxide (neutral, activity stage II) and then washed with chloroform. The oil obtained by concentrating the chloroform eluates by evaporation is dissolved in 640 ml of methylene chloride and, at a temperature of 3°–5°, 160 ml of an 8N chromium(VI) sulphuric acid solution are added over a period of 2 hours, and then the whole is stirred for 30 minutes while cooling with ice and for 2 hours at room temperature. The reaction mixture is diluted with methylene chloride and washed in succession with ice-cold dilute hydrochloric acid, ice-cold dilute sodium hydroxide solution and water, dried and concentrated by evaporation under a water-jet vacuum. The crude product is chromatographed over 50 times the amount of silica gel using a toluene/ethyl acetate (90:10) mixture.

5.92 ml of a 3.15N hydrochloric acid solution in isopropyl alcohol are added to 7.4 g of the resulting 3β,11α-dihydroxy-(5α)-20-spiroxan-21-one diacetate dissolved in 74 ml of methyl alcohol and 29.6 ml of methylene chloride and the whole is stirred for 6 hours at room temperature and then, after dilution with ice-water, extracted with chloroform. The organic phase is washed with water, dried, and concentrated by evaporation under a water-jet vacuum. The amorphous crude product is chromatographed over silica gel, there being obtained, using a toluene/acetone (90:10) mixture, 3β,11α-dihydroxy-(5α)-20-spiroxan-21-one 11-acetate that is pure according to thin-layer chromatography.

7 g of this monoacetate are dissolved in 350 ml of acetone and, while cooling with ice, 5.6 ml of an 8N chromium(VI) sulphuric acid solution are added at 5°–8° and the whole is stirred for 30 minutes while cooling with ice. After dilution with ice-water, extraction is carried out with chloroform, whereupon the organic phase is washed with ice-cold dilute sodium hydroxide solution, dried, and concentrated by evaporation under a water-jet vacuum.

8 g of the resulting 11α-hydroxy-(5α)-20-spiroxane-3,21-dione acetate are dissolved in 270 ml of methyl alcohol; a solution of 8 g of sodium hydroxide in 27 ml of water is added and the whole is boiled under reflux for 3 hours. After cooling to room temperature, a solution of 40 ml of concentrated hydrochloric acid in 27 ml of water is added and the whole is stirred vigorously for 30 minutes. After dilution with ice-water, extraction is carried out with chloroform, followed by drying and concentration by evaporation under a water-jet vacuum. The amorphous crude product is chromatographed over 50 times the amount of silica gel using a toluene/acetone (90:10) mixture, yielding 11α-hydroxy-(5α)-20-spiroxane-3,21-dione in pure form.

7.27 g of CuBr$_2$ are added to a solution, heated to 60°, of 5.82 g of 11α-hydroxy-(5α)-°-spiroxane-3,21-dione in 582 ml of tetrahydrofuran and the whole is stirred for 20 minutes at 60°. The reaction mixture is immediately poured onto 600 ml of ice-water and extracted twice with ethyl acetate. The organic phases are washed in succession with 10% potassium iodide solution, 10% sodium thiosulphate solution, ice-cold dilute sodium hydroxide solution, ice-cold dilute hydrochloric acid and with saturated sodium chloride solution, dried, and concentrated by evaporation at 40° under a water-jet vacuum. The crude product is chromatographed over 50 times the amount of silica gel using a toluene/acetone (90:10) mixture, yielding pure 2α-bromo-11α-hydroxy-(5α)-20-spiroxane-3,21-dione in amorphous form.

6 g of 2α-bromo-11α-hydroxy-(5α)-20-spiroxane-3,21-dione are dissolved in 60 ml of dimethylformamide; 3 g of lithium carbonate and 3 g of lithium bromide are added and the whole is boiled under reflux for 90 minutes. After cooling and dilution with ice-water, extraction is carried out twice with ethyl acetate. The organic phases are washed in succession with ice-cold dilute hydrochloric acid, ice-cold dilute sodium hydroxide solution and saturated sodium chloride solution, dried, and concentrated by evaporation under a water-jet vacuum. Using a toluene/acetone (90:10) mixture, there is eluted on 50 times the amount of silica gel 11α-hydroxy-(5α)-20-spirox-1-ene-3,21-dione which, after once dissolving and crystallising from methylene chloride/ether, melts at 279°–281°.

EXAMPLE 2

3.2 g of 9α,11α-epoxy-(5α)-20-spiroxane-3,21-dione are dissolved in 95 ml of dioxan; 3.2 g of 2,3-dichloro-5,6-dicyano-1,4-benzoquinone (DDQ) are added and the whole is stirred in a glass bomb tube for 16 hours at 140°. After concentration of the reaction mixture by evaporation, the crystalline residue is separated preparatively on 20 thick-layer chromatography plates (1 meter each) (eluant: toluene/acetone 75:25). The zone visible in UV light 254 nm yields, after elution with ethyl acetate, concentration of the solvent by evaporation and subsequent recrystallisation from methylene chloride/ether, 9α,11α-epoxy-(5α)-20-spirox-1-ene-3,21-dione having a melting point of 276°–278°.

EXAMPLE 3

1.9 g of 9α,11α-epoxy-(5α)-20-spiroxane-3,21-dione are dissolved in 76 ml of chlorobenzene; 1.9 g of benzeneseleninic acid anhydride are added and the whole is stirred for 2 hours at an external temperature of 80°. After cooling to room temperature, 100 ml of water are added and the whole is stirred for 30 minutes. The reaction solution is extracted with chloroform, whereupon the organic phase is washed in succession with ice-cold dilute hydrochloric acid and ice-cold dilute sodium hydroxide solution, dried over sodium sulphate and concentrated by evaporation under a water-jet vacuum. The crude product is chromatographed over 240 g of silica gel using methylene chloride/acetone 97:3. The resulting 9α,11α-epoxy-(5α)-20-spirox-1-ene-3,21-dione is dissolved and crystallised with methylene chloride/ether and has a melting point of 276°–278°.

EXAMPLE 4

A bromine solution consisting of 2.29 ml of bromine in 75 ml dioxan is added at room temperature over a period of 2 minutes to a solution of 0.75 g of 9α,11α-epoxy-(5α)-20-spiroxane-3,21-dione in 16.8 ml of dioxan and the whole is then stirred for a further 1 minute at room temperature. The reaction solution is poured onto 75 ml of ice-water containing 370 mg of sodium acetate trihydrate and extracted with ethyl acetate. The organic phase is washed with saturated sodium chloride solution, dried over sodium sulphate and concentrated by evaporation at a maximum of 40° under a water-jet vacuum. After the crude product has been dissolved in 8.25 ml of dimethylformamide, 280 mg of lithium carbonate and 280 mg of lithium bromide are added and the whole is boiled under reflux for 1.5 hours. 75 ml of ice-water containing 1.90 ml of concentrated hydrochloric acid are added to the cooled mixture and the whole is stirred for 10 minutes. After extraction twice with ethyl acetate, the organic phases are washed with saturated sodium chloride solution, dried and concentrated by evaporation. The crude product, chromatographed over 30 times the amount by weight of silica gel using a toluene/acetone (97:3) mixture, yields 9α,11α-epoxy-(5α)-20-spirox-1-ene-3,21-dione which, after once dissolving and crystallising from methylene chloride/ether, melts at 276°–278°.

EXAMPLE 5

2.14 g of 9α,11α-epoxy-(5α)-20-spirox-1-ene-3,21-dione are dissolved in 107 ml of tetrahydrofuran and, at room temperature, 6.44 ml of 0.84N aqueous potassium hydroxide solution are added over a period of approximately 1 minute and 21 ml of water are added over a period of approximately 2 minutes, and the whole is stirred for 18 hours at 50°. After cooling, 70 ml of water are added and the tetrahydrofuran is distilled off under a water-jet vacuum. After dilution with 200 ml of water, extraction is carried out three times using 200 ml of ether each time, the aqueous phase is frozen in a $CO_2$/acetone cooling bath and lyophilised under a high vacuum. Potassium 9α,11α-epoxy-17-hydroxy-3-oxo-5α,17α-pregn-1-ene 21-carboxylate is precipitated in flocculent form.

EXAMPLE 6

Tablets containing approximately 50 mg of active ingredient, for example 9α,11α-epoxy-(5α)-20-spirox-1-ene-3-one or 9α,11α-epoxy-(5α)-20-spirox-1-ene-3,21-dione, are manufactured as follows:

Composition for 1000 tablets active ingredient, very finely ground: 50.0 g
powdered sugar (saccharose): 79.0 g
gum arabic: 4.75 g
sorbitol: 3.75 g
talc: 2.5 g
magnesium stearate: 4.9 g
mineral oil: 0.1 g
carboxymethylcellulose (Na salt): 5.0 g Manufacture The active ingredient is mixed with the powdered sugar and the gum arabic, sieved and granulated by means of an approximately 35% aqueous sorbitol solution. The granulate is passed through a sieve of 3 mm mesh width and dried in a fluidised bed drier at 45°, sieved again and intimately mixed with the remaining adjuncts (talc, magnesium stearate, mineral oil and the sodium salt of carboxymethylcellulose). The mixture is pressed to form 150 mg tablets in the customary manner.

EXAMPLE 7

Gelatine capsules containing approximately 25 mg of active ingredient, for example 9α,11α-epoxy-(5α)-20-spirox-1-ene-3,21-dione, are manufactured as follows:

Composition for 1000 capsules active ingredient, very finely ground: 25 g
lactose, very finely ground: 25 g The active ingredient and the lactose are intimately mixed, triturated and sieved, and 50 mg portions of the resulting powder are introduced into gelatine capsules.

EXAMPLE 8

Tablets containing approximately 100 mg of component A and approximately 25 mg of component B are manufactured as follows:

| Composition of one tablet: | |
| --- | --- |
| component A, micronised | 100.0 mg |
| component B, micronised | 25.0 mg |
| maize starch | 50.0 mg |
| silica gel, colloidal | 5.0 mg |
| gelatine | 5.0 mg |
| cellulose, microcrystalline | 75.0 mg |
| sodium carboxymethyl starch | 20.0 mg |
| magnesium stearate | 1.5 mg |
| | 281.5 mg |

Manufacture of 100,000 tablets 10 kg of component A, micronised, and 2.5 kg of component B, micronised, and 5.0 kg of maize starch are mixed with 0.5 kg of colloidal silica, and processed with a solution of 0.5 kg of gelatine in 5.0 kg of distilled water (30° C.) to form a moist composition. This is passed through a sieve of 3 mm mesh width and dried at 45° C. (fluidised bed drier). The dry granulate is pressed through a sieve of 0.8 mm mesh width, mixed with a previously sieved mixture of 7.5 kg of microcrystalline cellulose and 2.0 kg of sodium carboxymethyl starch and 0.15 kg of magnesium stearate and pressed to form tablets each weighing 281.5 mg.

9α,11α-epoxy-(5α)-20-spirox-1-ene-3,21-dione is used as component A, and 6-chloro-7-sulphamyl-3,4-dihydro-1,2,4-benzothiadiazine 1,1-dioxide is used as component B.

In analogous manner, it is also possible to use the following active ingredients in appropriate amounts:

As component A: the potassium or sodium salt of 9α,11α-epoxy-17-hydroxy-3-oxo-5α,17α-pregn-1-ene-21-carboxylic acid (100 mg);

as component B: 2-chloro-5-(3-hydroxy-1-oxo-isoindolyl-3)-benzenesulphonamide (50 mg), 4-(2-methylenebutyryl)-2,3-dichlorophenoxyacetic acid (50 mg), (1-oxo-2-methyl-2-phenyl-6,7-dichloroindanyl-5-oxy)acetic acid (as racemate 20 mg, as the laevo-form 10 mg), or 3-cyclopentylmethyl-6-chloro-7-sulphamyl-3,4-dihydro-1,2,4-benzothiadiazine 1,1-dioxide (0.5 mg).

We claim:

1. (5α)-20-spirox-1-en-3-ones of the formula

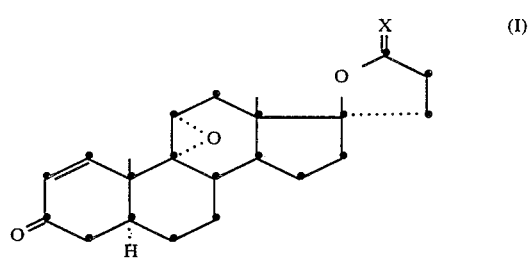

in which X represents O or $H_2$, and 17-hydroxy-5α,17α-pregn-1-en-3-ones of the formula

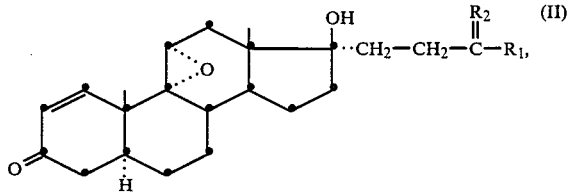

in which $R_2$ represents O and $R_1$ represents OH, OMe, OAlk, $NH_2$, $NHR_3$, $NR_3R_4$, or $R_2$ represents $H_2$ and $R_1$ represents OH, OAlk, OAr, OAralk or OAc, wherein $R_3$, $R_4$ and Alk represent lower alkyl, Me represents a metal atom or metal equivalent or the cation of an organic base, Ar represents monocyclic aryl, Aralk represents monocyclic aryl-lower alkyl, and Ac represents lower alkanoyl, monocyclic aroyl, lower alkylsulphonyl or monocyclic arylsulphonyl, it being possible for $R_3$ together with $R_4$ also to represent a lower alkylene group optionally interrupted by a hetero atom.

2. Compounds according to claim 1 in which Me represents an alkali or alkaline earth metal salt.

3. Compounds according to claim 1 in which Me represents an equivalent of an ammonium salt of an organic nitrogen-containing base.

4. Compounds according to claim 3 in which the ammonium salt is derived from a lower alkylamine, cycloalkylamine or benzylamine.

5. Compounds according to claim 4 in which the ammonium salt is derived from triethylamine, 2-hydroxy-ethylamine, di-(2-hydroxyethyl)-amine, tri-(2-hydroxy-ethyl)-amine, dicyclohexylamine, benzylamine, N',N'-dibenzylethylenediamine, pyridine, quinoline, N-ethyl-piperidine, morpholine or N,N'-dimethyl-piperazine.

6. Compounds of the formula (II) of claim 1 in which a "lower alkyl radical" in a substituent $R_1$ represents methyl, ethyl, n-propyl, isopropyl, n-butyl, isobutyl, tert.-butyl, n-pentyl or n-hexyl.

7. Compounds of the formula (II) of claim 1 in which a "lower alkanoyl group" in a substituent $R_1$ represents formyl, acetyl, propionyl, butyryl or valeroyl.

8. Compounds of the formula (II) of claim 1 in which "monocyclic aryl" in a substituent $R_1$ represents phenyl or the substitution derivatives thereof having from 1 to 3 lower alkyl groups and/or halogen atoms.

9. Compounds of the formula (II) of claim 1 in which "monocyclic aryl-lower alkyl" in a substituent $R_1$ represents phenylmethyl or phenylethyl.

10. Compounds of the formula (II) of claim 1 in which "monocyclic aroyl" in a substituent $R_1$ represents benzoyl, salicyloyl or anthranoyl.

11. Compounds of the formula (II) of claim 1 in which "monocyclic arylsulphonyl" in a substituent $R_1$ represents p-toluenesulphonyl or benzenesulphonyl, and "lower alkylsulphonyl" represents methyl- or ethyl-sulphonyl.

12. The compounds of the formula (II) of claim 1 in which a "lower alkylene group" $R_3R_4$ in a substituent $R_1$ has from 2 to 6 carbon atoms.

13. 9α,11α-epoxy-(5α)-20-spirox-1-ene-3,21-dione.

14. 9α,11α-epoxy-(5α)-20-spirox-1-en-3-one.

15. 9α,11α-epoxy-17-hydroxy-3-oxo-5α,17α-pregn-1-ene-21-carboxylic acid.

16. 9α,11α-epoxy-17-hydroxy-17α-(3-hydroxypropyl)-5α-androst-1-en-3-one.

17. The ethers and esters of 9α,11α-epoxy-17-hydroxy-17α-(3-hydroxypropyl)-3-one that are derived from lower alkanols having from 1 to 4 carbon atoms or from alkanoic acids having from 1 to 4 carbon atoms, respectively.

18. The esters of 9α,11α-epoxy-17-hydroxy-3-oxo-5α,17α-pregn-1-ene-21-carboxylic acid that are derived from alkanoic acids having from 1 to 4 carbon atoms.

19. The potassium, sodium or ammonium salt of 9α,11α-epoxy-17-hydroxy-3-oxo-5α,17α-pregn-1-ene-21-carboxylic acid.

20. The unsubstituted amide of 9α,11α-epoxy-17-hydroxy-3-oxo-5α,17α-pregn-1-ene-21-carboxylic acid and the mono- or di-methyl, -ethyl- or -propyl-amides.

21. A pharmaceutical composition according to claim 20 in which component B is selected from diuretics or saluretics from the group comprising benzothiazine, thiazide, hydrothiazide, benzenesulphonamide, phenoxyacetic acids, benzofuran-2-carboxylic acids and 2,3-dihydrobenzofuran-2-carboxylic acids.

22. A pharmaceutical composition containing
(a) an effective aldosterone-antagonistic amount of a compound according to claim 1, and
(b) at least one diuretic which promotes the increased excretion of sodium and potassium electrolytes.

23. A pharmaceutical composition according to claim 22 which contains one or more pharmaceutically acceptable carriers.

24. A pharmaceutical preparation containing an effective aldosterone-antagonistic amount of a compound according to claim 1, and one or more pharmaceutical acceptable carriers.

* * * * *

UNITED STATES PATENT AND TRADEMARK OFFICE
CERTIFICATE OF CORRECTION

PATENT NO. : 4,552,871

DATED : November 12, 1985

INVENTOR(S) : Jurgen Grob, and Jaroslav Kalvoda.

It is certified that error appears in the above-identified patent and that said Letters Patent is hereby corrected as shown below:

Column 30, Claim 21, line 2 should read -- according to claim 22 in which component B is selected from diuretics or --.

Signed and Sealed this

First Day of April 1986

[SEAL]

Attest:

DONALD J. QUIGG

Attesting Officer

Commissioner of Patents and Trademarks